US008008045B2

(12) United States Patent
Tanabe et al.

(10) Patent No.: US 8,008,045 B2
(45) Date of Patent: Aug. 30, 2011

(54) PRIMERS FOR ISOTHERMAL AMPLIFICATION OF HEPATITIS C VIRUS

(75) Inventors: Maiko Tanabe, Tokyo (JP); Chihiro Uematsu, Kawasaki (JP)

(73) Assignee: Hitachi High-Technologies Corporation, Tokyo (JP)

(*) Notice: Subject to any disclaimer, the term of this patent is extended or adjusted under 35 U.S.C. 154(b) by 355 days.

(21) Appl. No.: 11/976,232

(22) Filed: Oct. 23, 2007

(65) Prior Publication Data

US 2009/0191539 A1 Jul. 30, 2009

(51) Int. Cl.
*C12Q 1/68* (2006.01)
*C12P 19/34* (2006.01)

(52) U.S. Cl. ........... 435/91.2; 435/6; 435/6.1; 435/6.11; 435/6.12

(58) Field of Classification Search .................. None
See application file for complete search history.

(56) References Cited

U.S. PATENT DOCUMENTS

| 5,427,909 A | 6/1995 | Okamoto et al. |
| 6,174,868 B1 | 1/2001 | Anderson et al. |
| 6,297,048 B1 * | 10/2001 | Jolly et al. ................. 435/320.1 |

FOREIGN PATENT DOCUMENTS

| EP | 510952 A1 * | 10/1992 |
| JP | 09-075100 | 3/1997 |
| JP | 2004-135509 | 5/2004 |
| JP | 2004-329209 | 11/2004 |
| WO | WO 9315207 A2 * | 8/1993 |

OTHER PUBLICATIONS

Meng et al. (2001) Journal of Clinical Microbiology vol. 39 No. 8 pp. 2937-2945.*
Journal of General Virology (1993), 74, pp. 661-668.
Journal of General Virology (1992), 73, pp. 673-679.
Transfusion, vol. 33, pp. 7-13 (1993).
Journal of Clinical Microbiology, vol. 37, No. 8, pp. 2625-2630 (1999).
Pathology, 30(2), pp. 192-195 (1998).
Res. Virol., 149(4), pp. 219-227 (1998).
Journal of clinical Virology 29, pp. 84-91(2004).
M. Damen et al., Characterization of the Quantitative HCV NASBA Assay, Journal of Virological Methods, vol. 82, No. 1, Sep. 1999, pp. 45-54, XP002354402.
Rosalind Hollingsworth et al., Serum HCV RNA Levels Assessed by Quantitative NASBA®: Stability of Viral Load Over Time, and Lack of Correlation with Liver Disease, Journal of Hepatology, vol. 25, No. 3, 1996, pp. 301-306, XP002354403.
J. Saldanha et al., Establishment of the First International Standard for Nucleic Acid Amplification Technology (NAT) Assays for HCV RNA, Vox Sanguinis, vol. 76, No. 3, Apr. 1999, pp. 149-158, XP009005085.
Hollingsworth et al. (1996) J of Hepatology 25:301-306.
Damen et al. (1999) J of Virological Methods 82:45-54.
Saitoh et al. (2000) Nucleic Acids Symposium Series No. 44: 191-192.
Notice of Reasons for Rejection dated Sep. 15, 2009 in corresponding Japanese patent application No. 2004-149448.
H. Okamoto, et al.; The Journal of general virology, 1993, vol. 74, No. 11, p. 2385-2390.

* cited by examiner

*Primary Examiner* — Young J Kim
(74) *Attorney, Agent, or Firm* — Antonelli, Terry, Stout & Kraus, LLP.

(57) ABSTRACT

The present application relates to primers for isothermal amplification of HCV each include at least eighteen consecutive bases corresponding to a 3' end region of one selected from base sequences of SEQ ID NOs: 1-10, 21 and 22. The primers are specific to HCV subtypes 1a, 1b, 2a, 2b and 3a, respectively and enable genotyping of HCV by isothermal amplification.

3 Claims, 9 Drawing Sheets

KIND OF FLUOROPHORE ——: FAM (HCV SUBTYPE 1b)
▪▪▪▪: ROX (HCV SUBTYPE 2a)

FIG.9

HCV1a SEQUENCE (5'NTR~CORE REGION)

11~317 nt:5'NTR
318~914 nt:CORE REGION
318~676 nt:SUITABLE REGION FOR GENOTYPING

```
gccagccccc tgatgggggc gacactccac catgaatcac tcccctgtga ggaactactg    60
tcttcacgca gaaagcgtct agccatggcg ttagtatgag tgtcgtgcag cctccaggac   120
ccccctccc gggagagcca tagtggtctg cggaaccggt gagtacaccg gaattgccag    180
gacgaccggg tcctttcttg gatcaacccg ctcaatgcct ggagatttgg gcgtgccccc   240
gcaagactgc tagccgagta gtgttgggtc gcgaaaggcc ttgtggtact gcctgatagg   300  ~33
gtgcttgcga gtgccccggg aggtctcgta gaccgtgcac catgagcacg aatcctaaac   360
ctcaaaaaaa aaacaaacgt aacaccaacc gtcgcccaca ggacgtcaag ttcccgggtg   420
gcggtcagat cgttggtgga gtttacttgt tgccgcgcag gggccctaga ttgggtgtgc   480  ~34
gcgcgacgag aaagacttcc gagcggtcgc aacctcgagg tagacgtcag cctatcccca   540
aggctcgtcg gcccgagggc aggacctggg ctcagcccgg gtaccttgg cccctctatg    600
gcaatgaggg ctgcgggtgg gcgggatggc tcctgtctcc ccgtggctct cggcctagct   660
ggggccccac agaccccgg cgtaggtcgc gcaatttggg taaggtcatc gataccctta    720
cgtgcggctt cgccgacctc atggggtaca taccgctcgt cggcgcccct cttggaggcg   780
ctgccagggc cctggcgcat ggcgtccggg ttctggaaga cggcgtgaac tatgcaacag   840
ggaaccttcc tggttgctct ttctctatct tccttctggc cctgctctct tgcttgactg   900
tgcccgcttc ggcc                                                     914
```

PRIMERS FOR ISOTHERMAL AMPLIFICATION OF HEPATITIS C VIRUS

CLAIM OF PRIORITY

The present application claims priority from Japanese application JP 2004-149448 filed on May 19, 2004, the content of which is hereby incorporated by reference into this application.

FIELD OF THE INVENTION

The present invention relates to primers for isothermal amplification of subtypes of hepatitis C virus (hereinafter briefly referred to as "HCV"), and methods for detecting or determining HCV using the primers.

BACKGROUND OF THE INVENTION

Chiron Corporation, Emeryville, Calif. identified the gene of HCV in 1988. The genome sequence of HCV including about 9,500 bases has been identified, and it has been revealed that HCV has a single strand RNA as its genome. HCV is often accompanied with mutation in its gene sequence, is classified as four to six subgroups based on gene sequences in regions accompanied with frequent mutation, and is further classified as, for example, subtypes 1a, 1b, 2a, 2b and 3a (P. Simmonds, et al., J. Gen Virol., 74, 661-668 (1993))

Only two- to three-tenths of subjects infected with HCV have subjective symptoms such as malaise, and most of them undergo chronic inflammation without subjective symptoms and may further undergo liver cirrhosis and liver cancer. It is difficult to detect HCV at initial stage of HCV infection by immunoassay using antibodies and to prevent the symptoms from becoming worse and/or the infected blood completely from contaminating into blood for transfusion.

Recent years, however, have seen significant advances as a result of intensive studies and have enabled the detection of HCV infection and genotyping of HCV even at initial stage of HCV infection by a genetic test in which a gene is amplified. The genotyping enables determination of the incidence rate of acute hepatitis, the rate of becoming chronic and the possibility of shifting from hepatitis via liver cirrhosis to liver cancer, enables the prediction of efficacies of administration of an interferon selected depending on the subtype and enables the identification of contagion sources and infection route. Thus, the detection or determination of HCV by such a genetic test becomes superior to immunoassay.

Certain methods for genotyping HCV have been reported. Okamoto et al., for example, have reported a method for genotyping HCV, including the steps of preparing seven different primers using a core region of HCV as a target, and carrying out a reverse transcription polymerase chain reaction (RT-PCR) using a reverse transcriptase in combination with a suitable set of primers in J. Gen. Virol., 73, 673-679 (1992). A certain method for genotyping HCV in its NS5-region has been reported. Japanese Patent Application Laid-Open (JP-A) No. 09-75100 and F. McOmish, et al. in Transfusion, 33, 7-13 (1993) have reported a method including the steps of cleaving an amplified product of the 5'-untranslated region of HCV with a restriction enzyme and then genotyping HCV. Other methods for genotyping have been reported, including the steps of directly sequencing the amplified product just mentioned above, and genotyping HCV based on the resulting base sequence information [Germer J. J., et al., J. Clin. MiCrobiol., 37(8), 2625-2630 (1999); Holland J., et al., Pathology, 30(2), 192-195 (1998); and Doglio A., et al., Res. Virol., 149(4), 219-227 (1998)].

All the conventional oligonucleotide primers for genotyping HCV are to be amplified by PCR, and no oligonucleotide primer for genotyping HCV by isothermal amplification has been reported. This is probably because the HCV RNA has a complicated secondary structure as a result typically of intramolecular hydrogen bonds, a region that can be amplified by isothermal amplification is restricted, and it is very difficult to design specific primers capable of carrying out genotyping in the region. A method for quantitatively determining HCV by nucleic acid sequence-based amplification (NASBA), a kind of isothermal amplification, has been reported (Guichon A., et al., J. Clin. Virol., 29, 84-91 (2004)). This technique cannot determine the genotype of HCV gene although it can amplify the HCV gene. Specifically, all the conventional HCV genotyping techniques using oligonucleotide primers require complicated temperature control in PCR and invite complicated procedures, long time and high cost for the determination and are not satisfactory. Demands have therefore been made to develop oligonucleotide primers that enable genotyping of HCV by isothermal amplification.

SUMMARY OF THE INVENTION

Accordingly, an object of the present invention is to provide a technique for genotyping HCV by isothermal amplification. Another object of the present invention is to provide primers specific to HCV subtypes 1a, 1b, 2a, 2b and 3a for use in the technique.

The present inventors have successfully designed primers that enable genotype-specific isothermal amplification in a core region of gene sequences belonging to HCV subtypes 1a, 1b, 2a, 2b and 3a genes. The isothermal amplification of a HCV sample using these primers results in genotype-specific amplification and thereby enables detection and genotyping of HCV subtypes 1a, 1b, 2a, 2b and 3a genes based on whether or not amplification occurs.

Specifically, the present invention provides, in an aspect, a primer for isothermal amplification of HCV, comprising at least eighteen consecutive bases corresponding to a 3' end region of one base sequence selected from the group consisting of SEQ ID NOs: 1-10, 21 and 22.

The primer can further include a T7 promoter sequence in its 5'-end region typically when used in NASBA.

The present invention further provides, in another aspect, a pair of primers for isothermal amplification of hepatitis C virus, selected from the following pairs of primers (1) to (5):

(1) a pair of primers comprising at least eighteen consecutive bases corresponding to a 3' end region of the base sequences of SEQ ID NOs: 1 and 2, respectively;

(2) a pair of primers comprising at least eighteen consecutive bases corresponding to a 3' end region of the base sequences of SEQ ID NOs: 3 and 4, respectively, or a pair of primers comprising at least eighteen consecutive bases corresponding to a 3' end region of the base sequences of SEQ ID NOs: 3 and 9, respectively;

(3) a pair of primers comprising at least eighteen consecutive bases corresponding to a 3' end region of the base sequences of SEQ ID NOs: 5 and 6, respectively, or a pair of primers comprising at least eighteen consecutive bases corresponding to a 3' end region of the base sequences of SEQ ID NOs: 5 and 10, respectively;

(4) a pair of primers comprising at least eighteen consecutive bases corresponding to a 3' end region of the base sequences of SEQ ID NOs: 7 and 8, respectively; and (5) a pair of primers comprising at least eighteen consecutive bases corresponding to a 3' end region of the base sequences of SEQ ID NOs: 21 and 22, respectively.

When used typically in NASBA, at least one of the pair of primers can further include a T7 promoter sequence in its 5'-end region.

The present invention further provides, in yet another aspect, a method for detecting HCV, including the steps of subjecting a clinical sample to isothermal amplification with at least one of the pairs of primers according to the present invention, and determining a HCV subtype based on the resulting amplified product.

The method for detecting HCV enables determination of a HCV subtype. When isothermal amplification is carried out by NASBA, at least one of the pair of primers can further include a T7 promoter sequence.

The detection method of the present invention can simultaneously detect two or more HCV subtypes by using two or more pairs of primers of the present invention.

In addition and advantageously, the present invention provides a kit for use in the method for detecting HCV. The kit essentially includes at least one pair of primers of the present invention, and at least one probe containing a sequence complementary to an amplified product amplified by the action of the at least one pair of primers and serving to detect the amplified product and may further include, as needed, any of components that can be used in gene amplification and determination of amplified products, such as molecular weight markers, enzymes, dNTPs, NTPs and sterilized water, as well as any other components.

The primers of the present invention enable the detection and genotyping of a HCV subtype by isothermal amplification. The present invention therefore enables easy and rapid detection (determination) and genotyping of HCV without requiring complicated temperature control as in PCR.

Further objects, features and advantages of the present invention will become apparent from the following description of the preferred embodiments with reference to the attached drawings.

BRIEF DESCRIPTION OF THE DRAWINGS

FIG. 9 schematically illustrates the configuration of primers for isothermal amplification selective to the HCV subtype 1a gene.

DESCRIPTION OF THE PREFERRED EMBODIMENTS

Figure 1:
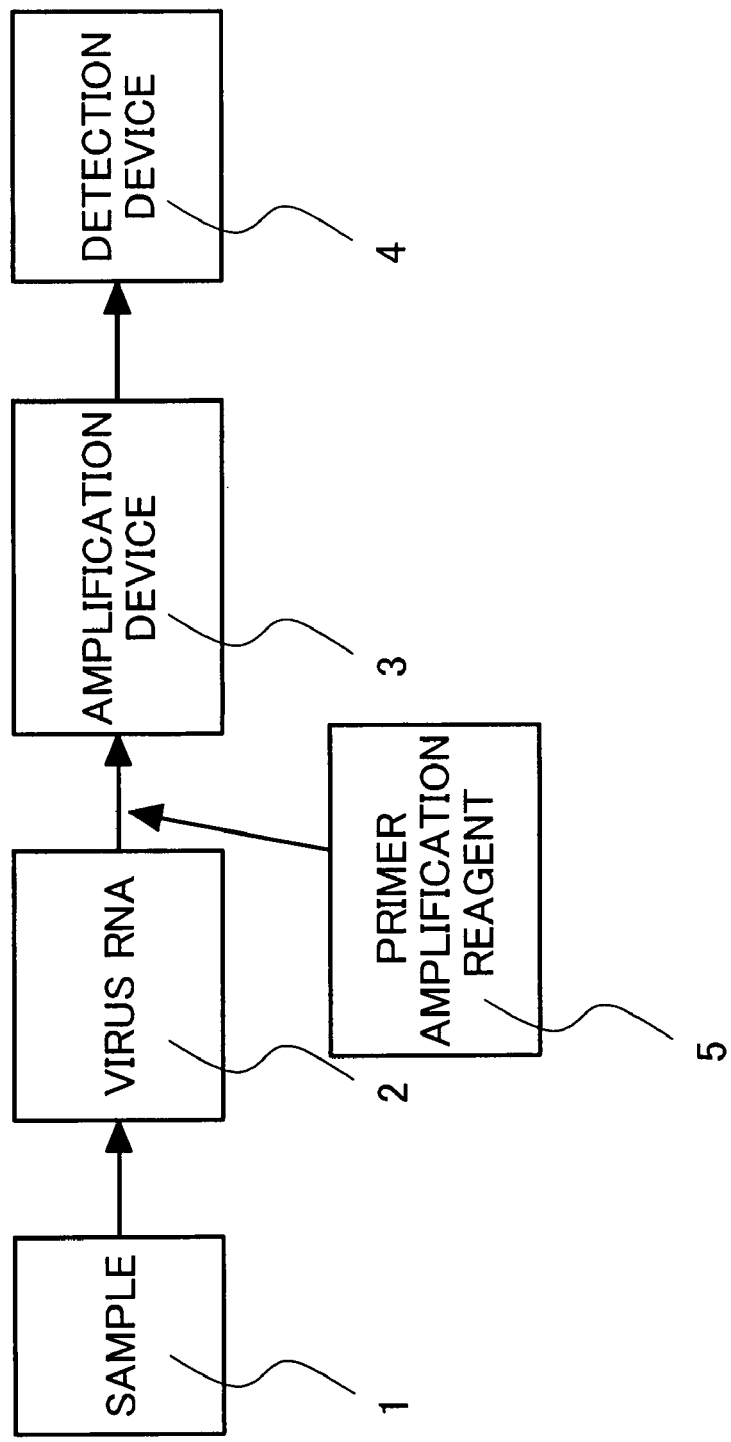
FIG. 1 is a flow chart of HCV genotyping.

1. Primers for Isothermal Amplification of HCV

The present inventors have designed various primers in specific regions (SEQ ID NOs: 40, 41, 42, 43 and 44, respectively) in the core regions of HCV subtypes 1a, 1b, 2a, 2b and 3a and determined whether or not each of the primers enables selective isothermal amplification of the corresponding subtype.

The designing of primers according to the present invention will be illustrated by taking HCV subtype 1a as an example. FIG. 9 shows the sequence of a region from the 5'-non-translated region (5'-NTR) to the core region of the HCV subtype 1a RNA. The region of 318th to 676th bases (SEQ ID NO: 40) in the sequence shown in FIG. 9 is a region suitable for genotyping. It has been revealed that primers having the sites 33 and 34 as priming sites, respectively, are optimal for HCV subtype 1a-specific isothermal amplification. Specifically, the primers corresponding to these priming sites have base sequences of SEQ ID NOs: 1 and SEQ ID NO: 2, respectively.

The sequences of subtype-specific primers for isothermal amplification determined in the same manner as above are shown in Table 1.

TABLE 1

Sequence of Oligonucleotides in This Invention

| Geno-type | SEQ ID NO | Sense or antisense | 5'-3' sequence |
|---|---|---|---|
| 1a | 1 | Sense | 5'-CACCATGAGCACGAATCCTA-3' |
|  | 2 | Antisense | 5'-WGCCTTGGGGATAGGCTG-3' |
| 1b | 3 | Sense | 5'-CACCATGAGCACGAATCCTA-3' |
|  | 4 | Antisense | 5'-GAGCCATCCTGCCCACCCCA-3' |
|  | 9 | Antisense | 5'-GGATAGGTTGTCGCCATCCA-3' |
| 2a | 5 | Sense | 5'-CCTAAACCTCAAAGAAAAACCA-3' |
|  | 6 | Antisense | 5'-TGGTTTTCCCCAGGATTTGCCAGT-3' |
|  | 10 | Antisense | 5'-CCCGTATAGGGGCCAGGGGTA-3' |
| 2b | 21 | Sense | 5'-AAGTTCCCGGGYGGCGGYCAGAT-3' |
|  | 22 | Antisense | 5'-ARCCCTCGTTTCCGTACAGRGGCCAA-3' |
| 3a | 7 | Sense | 5'-YAACATGAGCACACTTCCTA-3' |
|  | 8 | Antisense | 5'-TYCGCTCYGACGCGCCTTGGGGATA-3' |

As shown in Table 1, the oligonucleotides of SEQ ID NOs: 1 and 2 can be used as a sense primer and an antisense primer, respectively, in the amplification of HCV subtype 1a RNA. Likewise, the oligonucleotides of SEQ ID NOs: 3 and 4 or 9 can be used as a sense primer and an antisense primer, respectively, in the amplification of HCV subtype 1b RNA. The oligonucleotides of SEQ ID NOs: 5 and 6 or 10 can be used as a sense primer and an Io antisense primer, respectively, in the amplification of HCV subtype 2a RNA. The oligonucleotides of SEQ ID NOs: 21 and 22 can be used as a sense primer and an antisense primer, respectively, in the amplification of HCV subtype 2b RNA. The oligonucleotides of SEQ ID NOs: 7 and 8 can be used as a sense primer and an antisense primer, respectively, in the amplification of HCV subtype 3a RNA.

The sequences of primers for use in the present invention, however, are not limited to the above-listed sequences. It is also possible that a primer having several bases, e.g., about one to about five bases, preferably about one to three bases more or less than the above-specified sequence at the 5'-end of the corresponding primer, namely in a direction not the elongation direction of the primer, can enables isothermal amplification of the target HCV subtype 1a. The primer herein may not contain all the bases in the sequence and may include at least eighteen consecutive bases in its 3' end region for selective isothermal amplification of HCV subtype 1a.

Each of the primers of the present invention may further comprise, as needed, any of other sequences in its 5' end region, in addition to the template-specific sequence specifically hybridizing with a template represented by the sequence number. When the primer is used, for example, in NASBA (J. Compton: Nucleic acid sequence-based amplification. Nature, 1991, 350, p91-92), at least one of the pair of primers may have a T7 promoter sequence in its 5' end region. The primers may be appropriately modified typically with a labeling material such as a radioisotope, enzyme or fluorophore, and such modified primers are also included in the primers of the present invention.

The primers of the present invention preferably each have 18 to 30 bases in a region to hybridize with a template. The base length of the primers herein does not include the length of a region which does not hybridize with a template. For example, the T7 promoter sequence region of the primer for use in NASBA is not included in the base length of 18 to 30 bases.

The primers of the present invention may further comprise one to several base substitutions (mismatches for the template) within ranges not adversely affecting the advantages of the present invention. The primers should preferably include such mismatches (base substitutions) in their 5' end region, because base substitutions residing at the 3' end may adversely affect the precision of genotyping.

The primers of the present invention can be used in isothermal amplification such as NASBA, but can also be used in other primer extension amplification processes such as PCR (R. K. Saiki, et al., Science, 239, 487-491 (1988)), self-sustained sequence replication (3SR) (J. C. Guatelli, et al., Proc Natl Acad Sci USA, 87, 1874-1878 (1990)), and transcription-based amplification systems (TAS) (D. Y. Kwoh, et al., Proc Natl Acad Sci USA, 86, 1173-1177 (1989)).

2. Method for Detecting HCV (HCV Genotyping)

The present invention provides a method for detecting (genotyping) HCV by isothermal amplification with the primers. FIG. 1 is a flow chart of the method for detecting or genotyping HCV according to the present invention. In this method, a virus RNA 2 is extracted from a sample 1, is mixed with a primer amplification reagent 5, is amplified by an amplification device 3 and is detected by a detection device 4. The primer amplification reagent 5 contains an amplification reagent comprising dNTPs, NTPs and a buffer solution, and a primer mixture containing a primer of SEQ ID NO: 1, 3, 5, 7 or 21 in combination with a corresponding primer of SEQ ID NOs: 2, 4, 6, 8, 9, 10 or 22. The detection can be carried out, for example, by a method in which an amplified product is subjected to electrophoresis and lengths of amplified fragments (sizes of amplification) are compared, or a method of real-time detection of an amplified product typically using fluorophore-labeled probes.

Examples of isothermal amplification techniques for use in the present invention include LAMP (T. Notomi et al., Loop-mediated isothermal amplification of DNA. Nucleic Acids Res., 28(12): e63, (2000)) and ICAN (Isothermal and Chimeric Primer-initiated Amplification of Nucleic acids; Japanese Patent No. 3433929), in addition to above-mentioned NASBA.

The method for detecting HCV according to the present invention enables simultaneous detection of two or more HCV subtypes with two or more corresponding primers for isothermal amplification.

3. Kit for the Detection (Genotyping) of HCV

The present invention provides a kit for the detection (genotyping) of HCV. The kit essentially comprises all or part of the pairs of primers of the present invention, and one or more probes for detecting HCV subtype-specific amplified products amplified with the primers.

The probe for detecting a HCV subtype-specific amplified product is labeled with an appropriate labeling material such as a radioisotope, enzyme or fluorophore and comprises a sequence complementary to a sequence including about 18 to about 30 bases on a sample HCV gene fragment which is specifically amplified by the primer of the present invention. Examples of the probe are probes having base sequences of SEQ ID NOs: 19 and 20, respectively. When used as a molecular beacon probe, the probe may be labeled with a fluorophore such as FAM or ROX at one end and with a quencher such as BHQ1 or BHQ2 at the other end.

The kit for the detection (genotyping) of HCV of the present invention essentially comprises the primers and the probes and may further comprise, as needed, any of components that can be used in gene amplification and determination of amplified products, such as molecular weight markers, enzymes, dNTPs, NTPs and sterilized water, as well as any other components.

The present invention will be illustrated in further detail with reference to several examples below, which are never intended to limit the scope of the invention.

EXAMPLE 1

Screening of Primers Capable of Typing HCV Subtype 1a Gene by NASBA

An optimal pair of oligonucleotide primers for genotype-specific isothermal amplification by NASBA was determined by designing sense primers and antisense primers in regions in the core region of the HCV subtype 1a gene which are capable of highly specifically typing, setting pairs of the oligonucleotide primers in various combinations and subjecting the pairs of primers to NASBA. The sense primers are oligonucleotide primers of SEQ ID NOs: 1, 24, 25, 26, 27, 28, 29, 30, 31 and 32, and the antisense primers are oligonucleotide primers of SEQ ID NOs: 11, 33, 34, 35, 36, 37, 38 and 39 listed in Table 2. Each of the antisense primer further had a sequence (AATTCTAATACGACTCACTATAGGG AGAAGG: SEQ ID NO: 45) including a T7 promoter sequence at the 5' end.

TABLE 2

| Primer | Sequence* | location** | SEQ ID NO | Ref |
|---|---|---|---|---|
| HCV1p201 | 5'-GAGGTCTCGTAGACCGTGCACCA-3' (23 bp) | 2-25 bp | 24 | S1 |
| HCV1p202 | 5'-CACCATGAGCACGAATCCTA-3' (20 bp) | 21-40 bp | 1 | S2 |
| HCV1p203 | 5'-TCAGATCGTTGGTGGAGTTTA-3' (21 bp) | 108-127 bp | 25 | S3 |
| HCV1p204 | 5'-TCGTTGGTGGAGTTTACTTGTT-3' (22 bp) | 171-292 bp | 26 | S4 |
| HCV1p205 | 5'-AGGAAGACTTCCGAGCGGTC-3' (20 bp) | 172-291 bp | 27 | S5 |
| HCV1p206 | 5'-GGAAGACTTCCGAGCGGTCGCA-3' (22 bp) | 113-134 bp | 28 | S6 |
| HCV1p211 | 5'-CCTAAACCTCAAAGAAAAACCA-3' (22 bp) | 37-58 bp | 29 | S7 |
| HCV1p212 | 5'-CCAAACGTAACACCAACCGT-3' (20 bp) | 56-75 bp | 30 | S8 |
| HCV1p213 | 5'-AGTTCCCGGGTGGCGGTCAG-3' (20 bp) | 92-111 bp | 31 | S9 |
| HCV1p214 | 5'-AGACTTCCGAGCGGTCGCAAC-3' (21 bp) | 176-196 bp | 32 | S10 |
| HCV1p101 | 5'-AACTTGACGTCCTGTGGGCGA-3' (21 bp) | 75-95 bp | 33 | A1 |
| HCV1p102 | 5'-AAACTCCACCAACGATCTGA-3' (20 bp) | 108-127 bp | 34 | A2 |
| HCV1p103 | 5'-TGCCTTGGGGATAGGCTGGCGTCTA-3' (25 bp) | 204-228 bp | 35 | A3 |
| HCV1p104 | 5'-TGCCTTGGGGATAGGCTG-3' (18 bp) | 204-223 bp | 11(2) | A4 |
| HCV1p108 | 5'-ACGGTTGGTGTTACGTTTGG-3' (20 bp) | 56-75 bp | 36 | A5 |
| HCV1p109 | 5'-GGCGTCTACCTCGAGGTTGCG-3' (21 bp) | 191-111 bp | 37 | A6 |
| HCV1p112 | 5'-TACCTCGAGGTTGCGACCGCTCGGA-3' (25 bp) | 181-205 bp | 38 | A7 |
| HCV1p113 | 5'-GCCGACGTGCCTTGGGGA-3' (22 bp) | 218-239 bp | 39 | A8 |

*The sequences of the antisense primers A1 to A8 are exclusive of the T7 promoter sequence.
**The "Location" represents the location on SEQ ID NO: 40 where the primer is set.

Figure 2:
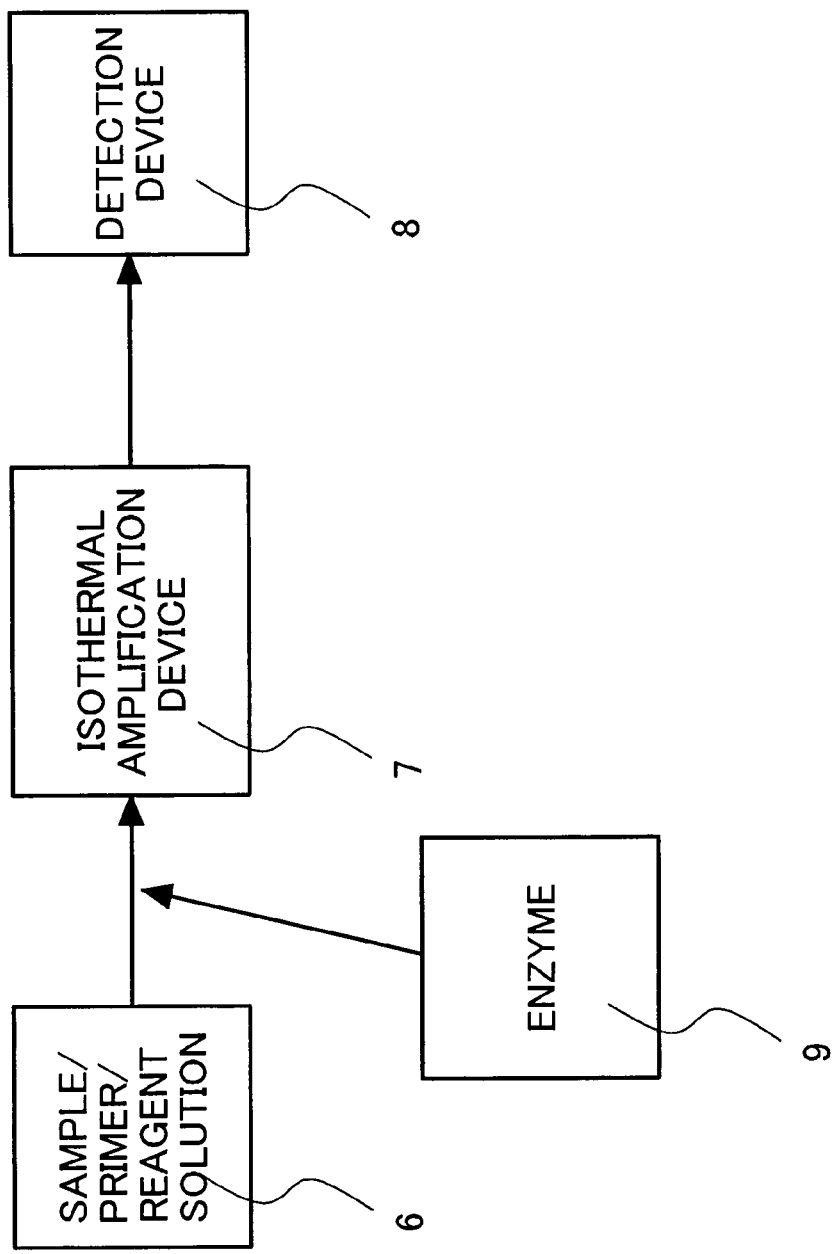
FIG. 2 is a flow chart of amplification by NASBA.

FIG. 2 is a flow chart of the amplification by NASBA. NASBA can be suitably carried out with a commercially available kit, such as NUCLISENS™ Basic Kit (bioMerieux, Inc.). A solution 6 for use in the reaction contains a HCV subtype 1a gene sample, a tested primer, reagents and other components. The solution 6 was subjected to a reaction by NASBA by holding the solution at 65° C. for 5 minutes and at 41° C. for 5 minutes; adding an enzyme 9 to the solution, followed by a reaction at 41° C. for 90 minutes in an isothermal amplification device 7. The resulting reaction product was detected with a detection device 8 by subjecting the reaction product to electrophoresis with SV1210 Cosmo-i (Hitachi High-Technologies Corporation) as the detection device 8 and determining the presence or absence of, and the position of the amplified product.

Figure 7:
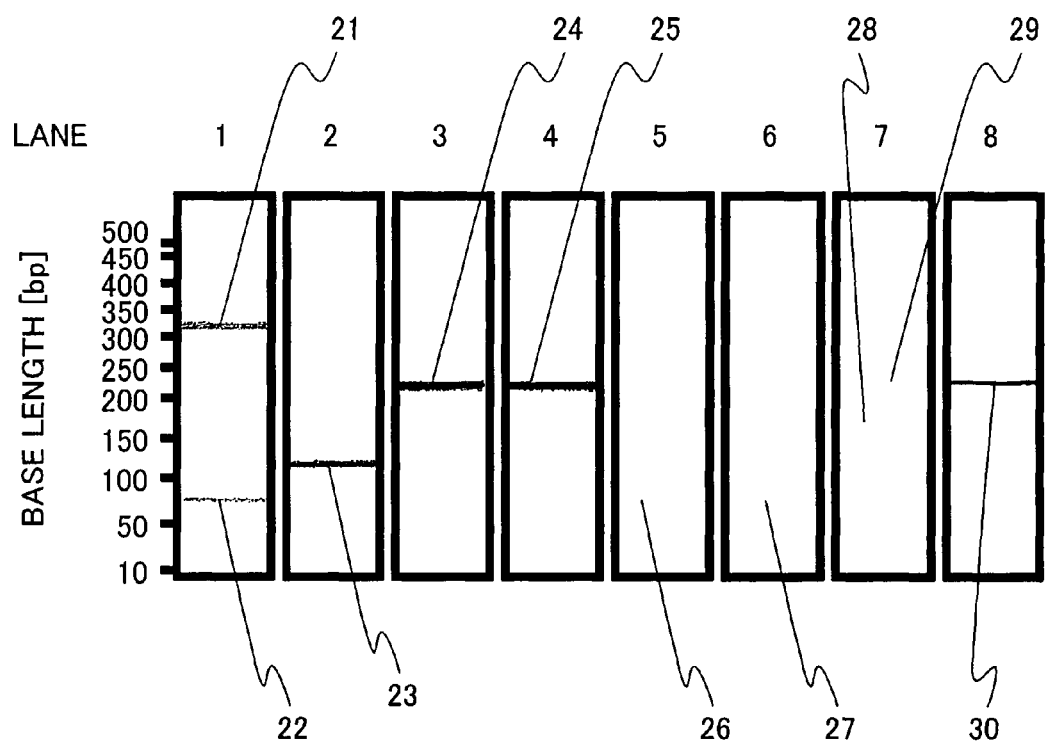
FIG. 7 shows an electropherogram obtained by the amplification of a HCV subtype 1a sample using oligonucleotide primers according to the present invention.

FIG. 7 shows an electropherogram of amplified products of amplification reaction using an oligonucleotide primer of SEQ ID NO: 1 as a sense primer, and those of SEQ ID NOs: 11, 33, 34, 35, 36, 37, 38 and 39 as an antisense primer, respectively. A pair of oligonucleotide primers of SEQ ID NOs: 1 and 11 was designed so as to yield, as a result of the reaction, an amplified product having a size of amplification of 217 bp. Likewise, pairs of oligonucleotide primers of SEQ ID NOs: 1 and 33, 1 and 34, 1 and 35, 1 and 36, 1 and 37, 1 and 38, and 1 and 39 were designed so as to yield amplified products having a size of amplification of 84 bp, 116 bp, 217 bp, 64 bp, 200 bp, 194 bp and 224 bp, respectively.

The product as a result of the reaction with the oligonucleotide primers of SEQ ID NOs: 1 and 33 was subjected to electrophoresis in Lane 1. Likewise, the reaction products as a result of the reactions of the oligonucleotide primers of SEQ ID NOs: 1 and 34, 1 and 35, 1 and 11, 1 and 36, 1 and 37, 1 and 38, and 1 and 39 were subjected to electrophoreses in Lanes 2, 3, 4, 5, 6, 7 and 8, respectively.

Amplified products 21 and 22 were detected at a base length of 317 bp and a base length of 78 bp, respectively, in Lane 1. Specifically, a non-specific amplified product was detected at another portion than at 78 bp which is in the vicinity of the set base length, 84 bp. An amplified product 23 was detected at a base length of 116 bp in Lane 2. An amplified product 24 was detected at a base length of 217 bp in Lane 3. An amplified product 25 was detected at a base length of 217 bp in Lane 4. An amplified product 26 was detected at a base length of 64 bp in Lane 5. In Lane 6, an amplified product 27 was detected at a base length of 51 bp. Namely, no amplified product was detected at a designed base length of 200 bp. In Lane 7, amplified products 28 and 29 were detected at a base length of 167 bp and a base length of 210 bp, respectively. Specifically, no amplified product was detected at the designed base length of 194 bp, but non-specific amplified products were detected at other positions. An amplified product 30 was detected at a base length of 224 bp in Lane 8.

These results show that the pairs of oligonucleotide primers corresponding to SEQ ID NOs: 1 and 33, 1 and 37, and 1 and 38 yielded non-specific amplified products (Lanes 1, 6 and 7), but the pairs of oligonucleotide primers corresponding to SEQ ID NOs: 1 and 34, 1 and 35, 1 and 36, 1 and 39, and 1 and 11 yielded specific amplified products to the HCV subtype 1a (Lanes 2, 3, 4, 5 and 8).

Next, the pairs of oligonucleotide primers corresponding to SEQ ID NOs: 1 and 34, 1 and 35, 1 and 36, 1 and 39, and 1 and 11, respectively, were subjected to determination of amplified products by NASBA using a HCV subtype 1b sample. This test was carried out to determine whether or not these oligonucleotide primers yield amplification specific only to the HCV subtype 1a gene, since they were designed so as to genotype the HCV subtype 1a gene and not to yield amplified products in the other subtypes.

Figure 8:
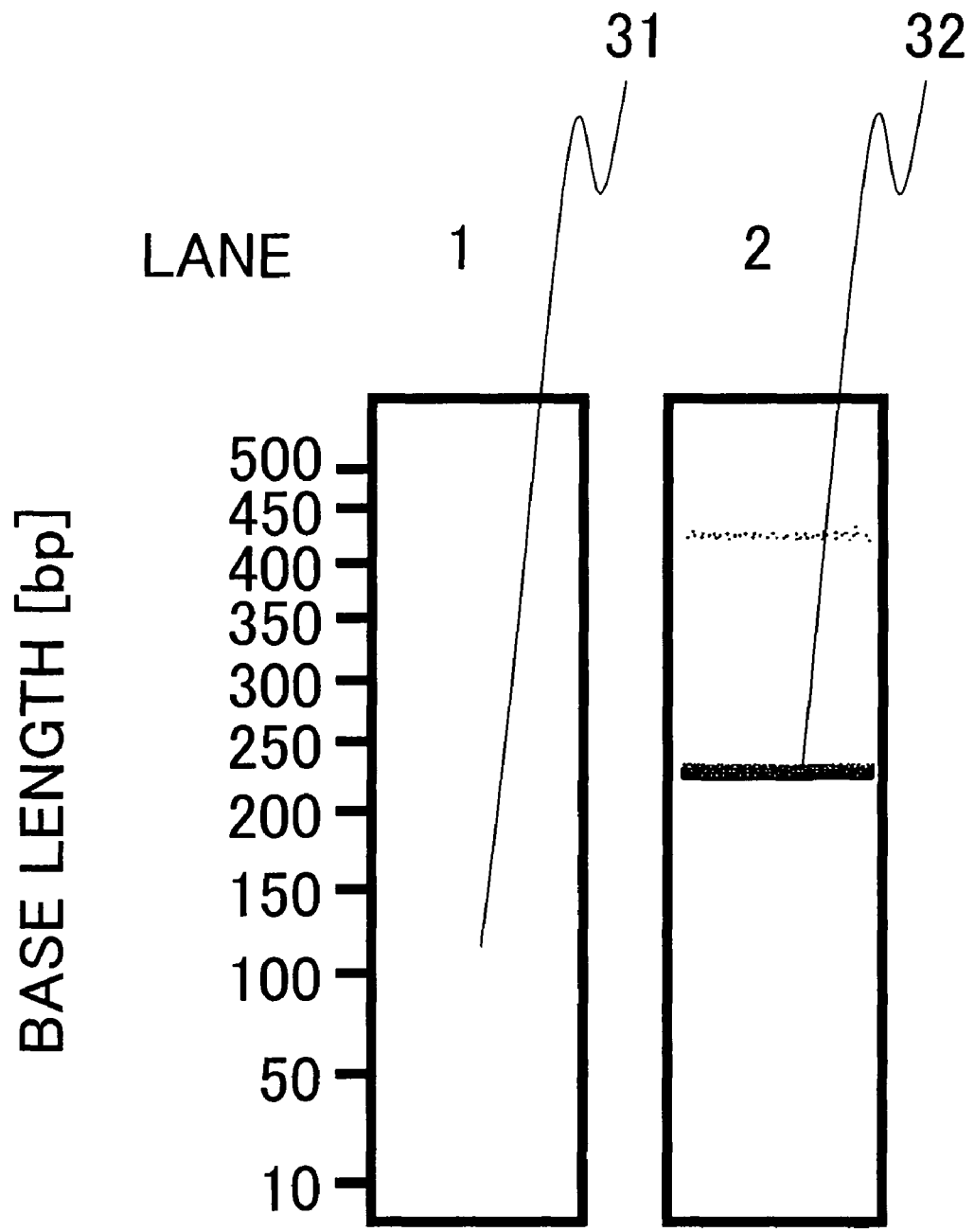
FIG. 8 shows an electropherogram obtained by the amplification of HCV subtype 1b sample using oligonucleotide primers of SEQ ID NOs: 1 and 11.

FIG. 8 shows an electropherogram of amplified products of amplification reaction of the HCV subtype 1b sample with the oligonucleotide primer of SEQ ID NO: 1 as a sense primer, and those of SEQ ID NOs: 11 and 39 as an antisense primer, respectively. The reaction products as a result of amplification of the subtype 1b sample with the pair of oligonucleotide primers corresponding to SEQ ID NOs: 1 and 11, and with the pair of oligonucleotide primers corresponding to SEQ ID NOs: 1 and 39 were subjected to electrophoresis in Lanes 1 and 2, respectively.

An amplified product 31 was detected at a base length of 100 bp in Lane 1. Namely, this pair of oligonucleotide primers yielded no amplified product in the case of the HCV subtype 1b sample at the designed base length of 217 bp, demonstrating that this pair specifically amplifies the HCV subtype 1a gene alone. An amplified product 32 was detected at a base length of 219 bp in Lane 2. This position of the amplified product is different from that of the HCV subtype 1a sample, at a base length of 224 bp, only by 5 bp, showing that this pair of oligonucleotide primers does not enable genotyping based on the base length of the amplified product. In contrast, the pair of oligonucleotide primers corresponding to SEQ ID NOs: 1 and 11 enables genotyping between the HCV subtype 1a and HCV subtype 1b genes based on the base length of the amplified product.

In the same way as above, whether or not amplified products by NASBA were detected at estimated base lengths was determined in samples of the other HCV subtypes, to find that the pair of oligonucleotide primers corresponding to SEQ ID NOs: 1 and 11 yields amplification specific to the HCV subtype 1a. The results are shown in Table 3.

TABLE 3

Size of Amplification and Assessment

| Sense | Antisense | Size (bp) of amplicon NASBA | Base length(bp) of the region sandwiched between the primers | Assessment* |
|---|---|---|---|---|
| S1 | A1 | 100 | 91 | x |
|  | A2 | 134 | 125 | x |
|  | A3 | 235 | 226 | x |
|  | A4 | 235 | 226 | x |
|  | A5 | 82 | 73 | x |
|  | A6 | 218 | 209 | x |
| S2 | A1 | 84 | 75 | x |
|  | A2 | 116 | 107 | Δ |
|  | A3 | 217 | 208 | Δ |
|  | A4 | 217 | 208 | ○ |
|  | A5 | 64 | 55 | Δ |
|  | A6 | 200 | 191 | x |
|  | A7 | 194 | 185 | x |
|  | A8 | 224 | 215 | Δ |
| S3 | A3 | 130 | 121 | x |
|  | A4 | 130 | 121 | x |
|  | A6 | 113 | 104 | x |
|  | A7 | 107 | 98 | x |
|  | A8 | 137 | 128 | Δ |
| S4 | A3 | 125 | 116 | x |
|  | A4 | 125 | 116 | x |
|  | A6 | 108 | 99 | x |
| S5 | A3 | 66 | 57 | x |
|  | A4 | 66 | 57 | x |
| S6 | A3 | 65 | 56 | x |
|  | A4 | 65 | 56 | x |

TABLE 3-continued

Size of Amplification and Assessment

| Sense | Antisense | Size (bp) of amplicon NASBA | Base length(bp) of the region sandwiched between the primers | Assessment* |
|---|---|---|---|---|
| S7 | A1 | 68 | 59 | x |
|  | A2 | 100 | 91 | x |
|  | A3 | 201 | 192 | x |
|  | A4 | 201 | 192 | Δ |
|  | A6 | 184 | 175 | x |
|  | A7 | 178 | 169 | x |
|  | A8 | 208 | 199 | x |
| S8 | A2 | 81 | 72 | x |
|  | A3 | 183 | 174 | x |
|  | A4 | 183 | 174 | x |
|  | A6 | 165 | 156 | x |
| S9 | A3 | 62 | 53 | x |
|  | A4 | 146 | 137 | x |
|  | A6 | 129 | 120 | x |
|  | A7 | 121 | 112 | x |
|  | A8 | 151 | 142 | x |
| S10 | A3 | 62 | 53 | x |
|  | A4 | 62 | 53 | x |
|  | A8 | 67 | 58 | Δ |

*Criteria for Assessment:
Good(○): Primer capable of genotyping
Fair(Δ): Primer capable of amplifying but incapable of genotyping
Failure(x): Primer incapable of amplifying Table 3 shows that the pair of oligonucleotide primers corresponding to SEQ ID NOs: 1 and 11 is suitable for the genotyping of the HCV subtype 1a gene. The sense primer corresponding to SEQ ID NO: 1 is considered to be capable of isothermally amplifying the HCV subtype 1a even if the priming site is narrowed by about two bases or less, or extended by about five bases or less at the 5' end and to be capable of genotyping the HCV subtype 1a even if the priming site is narrowed by about one or two bases at the 5' end. The antisense primer corresponding to SEQ ID NO: 11 is considered to be capable of isothermally amplifying the HCV subtype 1a even if the priming site is extended by about twelve bases or less at the 5' end and to be capable of genotyping the HCV subtype 1a even if the priming site is extended by about five bases or less at the 5' end.

EXAMPLE 2

Screening of Primers Capable of Genotyping HCV Subtypes 1b, 2a, 2b and 3a

Optimal pairs of oligonucleotide primers for genotype-specific isothermal amplification of HCV subtypes 1b, 2a, 2b and 3a genes by NASBA were determined by the procedure of Example 1.

(1) HCV Subtype 1b Gene

Primers listed in Table 4 were designed based on the sequence of a specific region capable of typing the core region of the HCV subtype 1b gene (SEQ ID NO: 41 corresponding to 1 to 325 bp of the core region of HCV subtype 1b). Different pairs of these primers were subjected to isothermal amplification by NASBA under the same conditions as in Example 1 using, as a template, a HCV subtype 1b gene sample, and the presence or absence of, and the position of amplified product were determined by electrophoresis. In addition, the presence or absence of, and the position of amplified product by NASBA using samples of the other HCV subtypes were determined on pairs of primers which yielded the amplified product so as to determine whether or not the pairs of primers are capable of genotyping the HCV subtype 1b gene. The set primer regions and results are shown in Table 4.

TABLE 4

| Primer | Position on SEQ ID NO: 41* | Assessment** | Remarks |
|---|---|---|---|
| HCV2p201 | 21-40 bp | ○ | Corresponding to SEQ ID Nos: 3 and 17 |
| HCV2p202 | 37-58 bp | Δ | |
| HCV2p203 | 92-111 bp | x | |
| HCV2p204 | 108-127 bp | x | |
| HCV2p205 | 192-219 bp | x | |
| HCV2p101 | 191-214 bp | Δ | |
| HCV2p102 | 201-220 bp | ○ | Corresponding to SEQ ID No: 9 |
| HCV2p103 | 242-260 bp | x | |
| HCV2p104 | 296-305 bp | ○ | Corresponding to SEQ ID Nos: 4 and 12 |

*The position represents the position of set primer on SEQ ID NO: 41
**Criteria for Assessment:
Good(○): Primer capable of genotyping
Fair(Δ): Primer capable of amplifying but incapable of genotyping
Failure(x): Primer incapable of amplifying Table 4 shows that the oligonucleotide primers corresponding to SEQ ID NOs: 3, 4 and 9 are suitable for the genotyping of the HCV subtype 1b gene. The sense primer corresponding to SEQ ID NO: 3 is considered to be capable of isothermally amplifying the HCV subtype 1b gene even if the priming site is narrowed by about two bases or less, or extended by about five bases or less at the 5' end and to be capable of genotyping the HCV subtype 1b gene even if the priming site is narrowed by about one or two bases at the 5' end. The antisense primer corresponding to SEQ ID NO: 4 or 9 is considered to be capable of isothermally amplifying the HCV subtype 1b gene even if the priming site is extended by about ten bases or less at the 5' end and to be capable of genotyping the HCV subtype 1b gene even if the priming site is extended by about six bases or less at the 5' end.

(2) HCV Subtype 2a Gene

Primers listed in Table 5 were designed based on the sequence of a specific region capable of typing the core region of the HCV subtype 2a gene (SEQ ID NO: 42 corresponding to 21 to 295 bp of the core region of HCV subtype 2a). Different pairs of these primers were subjected to isothermal amplification by NASBA under the same conditions as in Example 1 using, as a template, a HCV subtype 2a gene sample, and the presence or absence of, and the position of amplified product were determined by electrophoresis. In addition, the presence or absence of, and the position of amplified product by NASBA using samples of the other HCV subtypes were determined on pairs of primers which yielded the amplified product so as to determine whether or not the pairs of primers are capable of genotyping the HCV subtype 2a gene. The set primer regions and results are shown in Table 5.

TABLE 5

| Primer | Position on SEQ ID NO: 42* | Assessment** | Remarks |
|---|---|---|---|
| HCV3p201 | 21-40 bp | x | |
| HCV3p202 | 37-58 bp | ○ | Corresponding to SEQ ID Nos: 5 and 18 |
| HCV3p203 | 41-63 bp | x | |
| HCV3p204 | 55-78 bp | x | |
| HCV3p205 | 88-106 bp | x | |
| HCV3p206 | 151-175 bp | x | |
| HCV3p207 | 151-174 bp | x | |

TABLE 5-continued

| Primer | Position on SEQ ID NO: 42* | Assessment** | Remarks |
|---|---|---|---|
| HCV3p101 | 202-227 bp | x | |
| HCV3p102 | 217-240 bp | ○ | Corresponding to SEQ ID Nos: 6 and 13 |
| HCV3p103 | 242-260 bp | ○ | Corresponding to SEQ ID No: 10 |

*The position represents the position of set primer on SEQ ID NO: 42
**Criteria for Assessment:
Good(○): Primer capable of genotyping
Fair(Δ): Primer capable of amplifying but incapable of genotyping
Failure(x): Primer incapable of amplifying Table 5 shows that the oligonucleotide primers corresponding to SEQ ID NOs: 5, 6 and 10 are suitable for the genotyping of the HCV subtype 2a gene. The sense primer corresponding to SEQ ID NO: 5 is considered to be capable of isothermally amplifying and genotyping the HCV subtype 2a gene even if the priming site is narrowed by about four bases or less, or extended by about three bases or less at the 5' end. The antisense primer corresponding to SEQ ID NO: 6 or 10 is considered to be capable of isothermally amplifying the HCV subtype 2a gene even if the priming site is narrowed by about four bases or less, or extended by about eight bases or less at the 5' end and to be capable of genotyping the HCV subtype 2a gene even if the priming site is narrowed by about four bases or less or extended by about one base or less at the 5' end.

(3) HCV Subtype 2b Gene

Primers listed in Table 6 were designed based on the sequence of a specific region capable of typing the core region of the HCV subtype 2b gene (SEQ ID NO: 43 corresponding to 1 to 305 bp of the core region of HCV subtype 2b). Different pairs of these primers were subjected to isothermal amplification by NASBA under the same conditions as in Example 1 using, as a template, a HCV subtype 2b gene sample, and the presence or absence of, and the position of amplified product were determined by electrophoresis. In addition, the presence or absence of, and the position of amplified product by NASBA using samples of the other HCV subtypes were determined on pairs of primers which yielded the amplified product so as to determine whether or not the pairs of primers are capable of genotyping the HCV subtype 2b gene. The set primer regions and results are shown in Table 6.

TABLE 6

| Primer | Position on SEQ ID NO: 43* | Assessment** | Remarks |
|---|---|---|---|
| HCV4p201 | 16-40 bp | x | |
| HCV4p202 | 37-58 bp | Δ | |
| HCV4p203 | 21-40 bp | x | |
| HCV4p204 | 91-113 bp | ○ | Corresponding to SEQ ID Nos: 21 and 23 |
| HCV4p205 | 92-110 bp | Δ | |
| HCV4p206 | 108-132 bp | Δ | |
| HCV4p101 | 210-235 bp | Δ | |
| HCV4p102 | 241-257 bp | Δ | |
| HCV4p103 | 244-264 bp | x | |
| HCV4p104 | 270-295 bp | ○ | Corresponding to SEQ ID No: 22 |

*The position represents the position of set primer on SEQ ID NO: 43
**Criteria for Assessment:
Good(○): Primer capable of genotyping
Fair(Δ): Primer capable of amplifying but incapable of genotyping
Failure(x): Primer incapable of amplifying Table 6 shows that the oligonucleotide primers corresponding to SEQ ID NOs: 21 and 22 are suitable for the genotyping of the HCV subtype 2b gene. The sense primer corresponding to SEQ ID NO: 21 is considered to be capable of isothermally amplifying the HCV subtype 2b gene even if the priming site is narrowed by about two bases or less, or extended by about seventeen bases or less at the 5' end and to be capable of genotyping the HCV subtype 2b gene even if the priming site is narrowed by about two bases or less at the 5' end. The antisense primer corresponding to SEQ ID NO: 22 is considered to be capable of isothermally amplifying the HCV subtype 2b gene even if the priming site is narrowed by about five bases or less at the 5' end and to be capable of genotyping the HCV subtype 2b gene even if the priming site is narrowed by about five bases or less at the 5' end.

(4) HCV Subtype 3a Gene

Primers listed in Table 7 were designed based on the sequence of a specific region capable of typing the core region of the HCV subtype 3a gene (SEQ ID NO: 44 corresponding to 1 to 366 bp of the core region of HCV subtype 3a). Pairs of these primers were subjected to isothermal amplification by NASBA under the same conditions as in Example 1 using, as a template, a HCV subtype 3a gene sample, and the presence or absence of, and the position of amplified product were determined by electrophoresis. In addition, the presence or absence of, and the position of amplified product by NASBA using samples of the other HCV subtypes were determined on pairs of primers which yielded the amplified product so as to determine whether or not the pairs of primers are capable of genotyping the HCV subtype 3a gene. The set primer regions and results are shown in Table 7.

TABLE 7

| Primer | Position on SEQ ID NO: 44* | Assessment** | Remarks |
|---|---|---|---|
| HCV5p201 | 21-40 bp | ○ | Corresponding to SEQ ID No: 7 |
| HCV5p202 | 37-58 bp | Δ | |
| HCV5p203 | 61-81 bp | x | |
| HCV5p204 | 91-111 bp | x | |
| HCV5p205 | 109-133 bp | Δ | |
| HCV5p206 | 171-195 bp | x | |
| HCV5p101 | 216-240 bp | ○ | Corresponding to SEQ ID Nos: 8 and 14 |
| HCV5p102 | 227-245 bp | Δ | |
| HCV5p103 | 244-267 bp | Δ | |
| HCV5p104 | 270-288 bp | x | |
| HCV5p105 | 285-304 bp | Δ | |
| HCV5p106 | 340-356 bp | x | |

*The position represents the position of set primer on SEQ ID NO: 44
**Criteria for Assessment:
Good(○): Primer capable of genotyping
Fair(Δ): Primer capable of amplifying but incapable of genotyping
Failure(x): Primer incapable of amplifying Table 7 shows that the oligonucleotide primers corresponding to SEQ ID NOs: 7 and 8 are suitable for the genotyping of the HCV subtype 3a gene. The sense primer corresponding to SEQ ID NO: 7 is considered to be capable of isothermally amplifying the HCV subtype 3a gene even if the priming site is narrowed by about two bases or less, or extended by about five bases or less at the 5' end and to be capable of genotyping the HCV subtype 3a gene even if the priming site is narrowed by about two bases or less at the 5' end. The antisense primer corresponding to SEQ ID NO: 8 is considered to be capable of isothermally amplifying and genotyping the HCV subtype 3a gene even if the priming site is narrowed by about five bases or less at the 5' end.

EXAMPLE 3

Genotyping of HCV subtypes 1a, 1b, 2a, 2b and 3a genes by NASBA

Genotyping of HCV was carried out by isothermal amplification according to NASBA and electrophoresis by the procedure of Example 1. More specifically, the sense primers used are oligonucleotide primers corresponding to SEQ ID NOs: 1, 3, 5 and 7, and the antisense primers are oligonucleotide primers corresponding to SEQ ID NOs: 11, 12, 13 and 14 each further having a sequence including a T7 promoter sequence at the 5' end.

A pair of oligonucleotide primers corresponding to SEQ ID NOs: 1 and 2 was so designed as to yield an amplified product having a size of 217 bp as a result of the amplification of a sample HCV subtype 1a RNA. Likewise, a pair of oligonucleotide primers corresponding to SEQ ID NOs: 3 and 4, a pair of oligonucleotide primers corresponding to SEQ ID NOs: 5 and 6, and a pair of oligonucleotide primers corresponding to SEQ ID NOs: 7 and 8 were so designed as to yield amplified products having sizes of 209 bp, 234 bp and 229 bp as a result of the amplification of HCV subtype 1b RNA sample, HCV subtype 2a RNA sample, and HCV subtype 3a RNA sample respectively.

Figure 3:
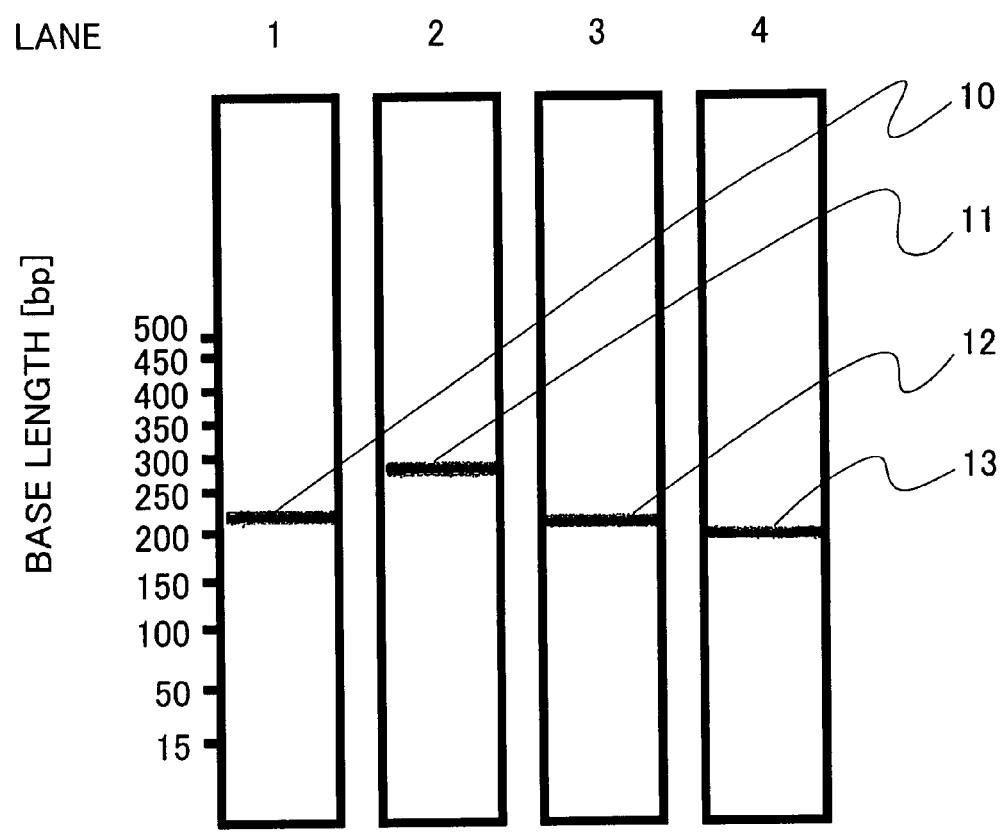
FIG. 3 shows an electropherogram obtained by genotyping of HCV samples using oligonucleotide primers of the present invention.

FIG. 3 shows the resulting electropherogram. Amplified products 10, 11, 12 and 13 in Lanes 1, 2, 3 and 4 as a result of amplification of the HCV subtypes 1a, 1b, 2a and 3a RNA samples were detected at base lengths of 217 bp, 304 bp, 234 bp and 229 bp, respectively. In other words, the samples of HCV subtypes 1a, 1b, 2a and 3a RNAs yield amplified products having different sizes of amplification of 217 bp, 304 bp, 234 bp and 229 bp, respectively, with the oligonucleotide primers capable of carrying out genotype-specifically amplification.

These results show that the amplified product as a result of isothermal amplification of the HCV subtype 1a RNA with the pair of oligonucleotide primers corresponding to SEQ ID NOs: 1 and 2 is positioned at the estimated length of the amplified gene, and that those of the other HCV subtypes 1b, 2a and 3a samples were positioned at the estimated lengths of the amplified genes. Namely, it is verified that the oligonucleotide primers according to the present invention are capable of genotyping of HCV subtypes.

EXAMPLE 4

Real-Time Detection of HCV Subtypes 1b and 2a Genes by NASBA with Molecular Beacon HCV subtypes 1b and 2a, which invite many infections in Japan, were genotyped with a real-time detection device. For selective real-time detection, oligonucleotide primers corresponding to SEQ ID NOs: 15 and 16, which correspond to oligonucleotide primers of SEQ ID NOs: 9 and 10, except with a Tag sequence added at the 5' end, were used as antisense primers, and oligonucleotide primers corresponding to SEQ ID NO: 17 and 18, which correspond to oligonucleotide primers of SEQ ID NOs: 3 and 5, except with a T7 promoter added at the 5' end, were used as sense primers.

Molecular beacon probes (S. Tyagi, et al., Nature Biotechnol, 14, 303-308(1996)) were used as a probe in the real-time detection. The molecular beacon probes were designed so as to have a Tag sequence and base sequences corresponding to SEQ ID NOs: 19 and 20, respectively, for distinguishing the Tag sequence. The molecular beacon corresponding to SEQ ID NO: 19 was modified with FAM as a fluorophore and with BHQ1 as a quencher. The molecular beacon corresponding to SEQ ID NO: 20 was modified with ROX as a fluorophore and with BHQ2 as a quencher.

The sample HCV gene was amplified by NASBA by the procedure of Example 1, except for using NUCLISENS™ Basic Kit (bioMerieux, Inc.).

Figure 4:
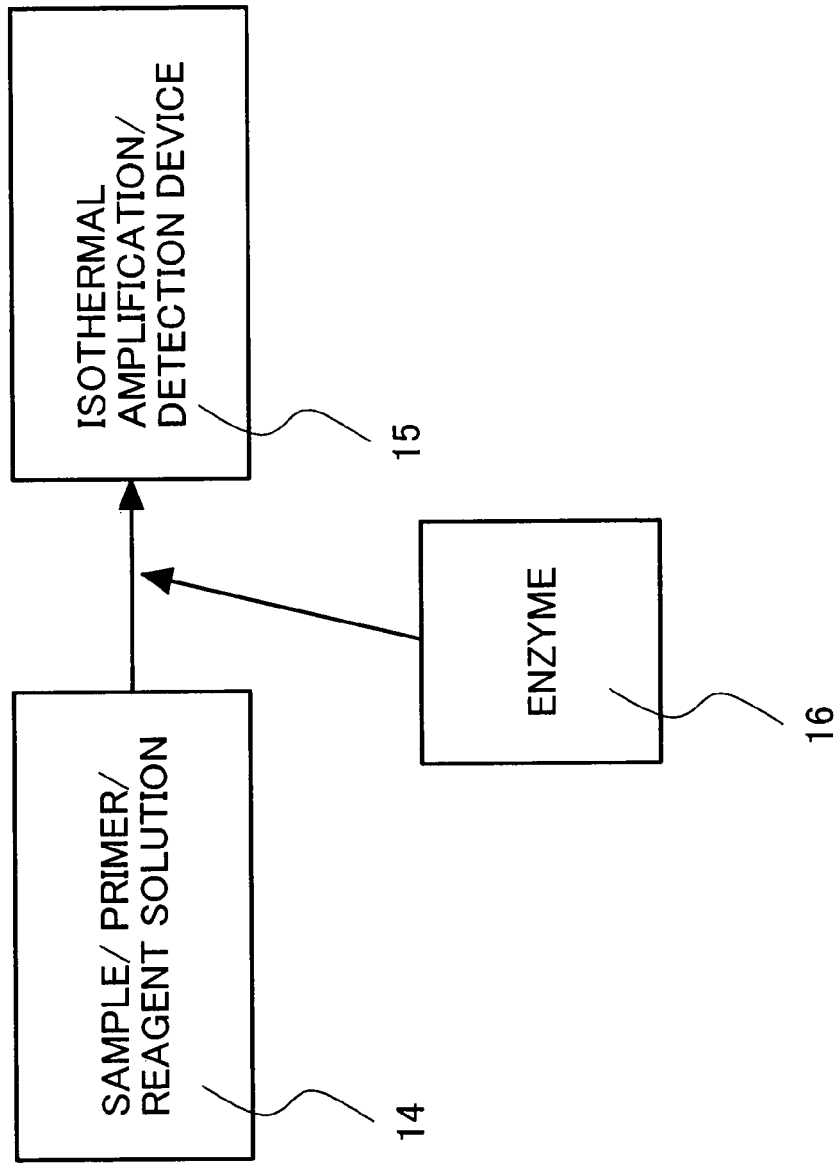
FIG. 4 is a flow chart of real-time genotyping of HCV gene.
Figure 5A:
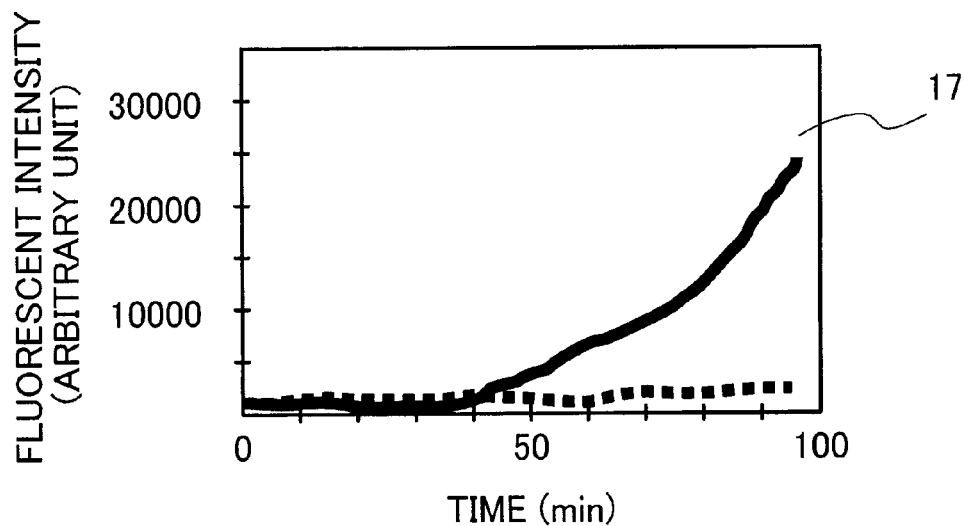
FIGS. 5A and 5B illustrate real-time genotyping of HCV using oligonucleotide primers according to the present invention using a HCV RNA of subtype 1b and a HCV RNA of subtype 2a as a sample, respectively.
Figure 5B:
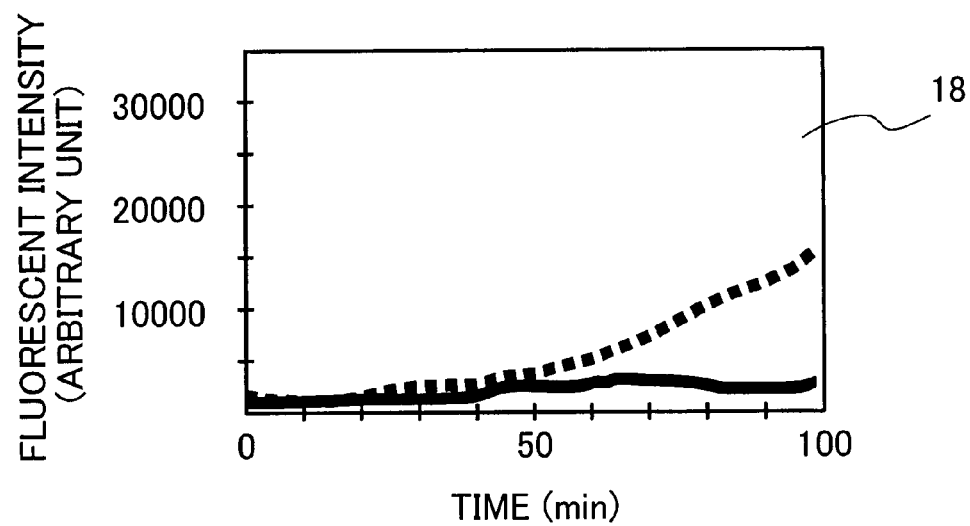

FIG. 4 is a flow chart of real-time detection (genotyping) of the HCV gene. Specifically, a solution 14 containing, for example, a sample, primers and reagents was mixed with an enzyme 16, was subjected to amplification, and the amplified product was detected in real-time in an isothermal amplification/detection device 15. The isothermal amplification/detection device 15 used herein was Mx 3000p (Stratagene). The results are shown in FIGS. 5A and 5B. FIGS. 5A and 5B show results 17 and 18 in which a HCV subtype 1b gene RNA and a HCV subtype 2a gene RNA as samples were amplified, respectively, with the ordinate indicating the fluorescent intensity and the abscissa indicating the time. In the figures, the fluorescent intensity of FAM capable of identifying the HCV subtype 1b amplified product is indicated by solid lines, and the fluorescent intensity of ROX capable of identifying the HCV subtype 2a amplified product is indicated by dashed lines. FIG. 5A shows that only the fluorescent intensity of FAM increases with time, indicating that the sample is of the HCV subtype 1b. In contrast, FIG. 5B shows that only the fluorescence intensity of ROX increases with time, indicating that the sample herein is of the HCV subtype 2a. These results show that the oligonucleotide primers of the present invention do not interfere with amplification with another primer and are sufficiently accurately usable in the amplification, that they can easily genotype HCV subtypes based on the kind of fluorophore and can quantitatively determine the HCV subtypes by measuring the rise time of fluorescent intensity.

EXAMPLE 5

Simultaneous Detection of HCV Subtypes 1b and 2b by NASBA

HCV genotyping was carried out using oligonucleotide primers corresponding to SEQ ID NOs: 3 and 21 as sense primers, and oligonucleotide primers corresponding to SEQ ID NOs: 12 and 23 as antisense primers. The antisense primers correspond to SEQ ID NOs: 4 and 22, except for further having a T7 promoter sequence at the 5' end.

Figure 6:
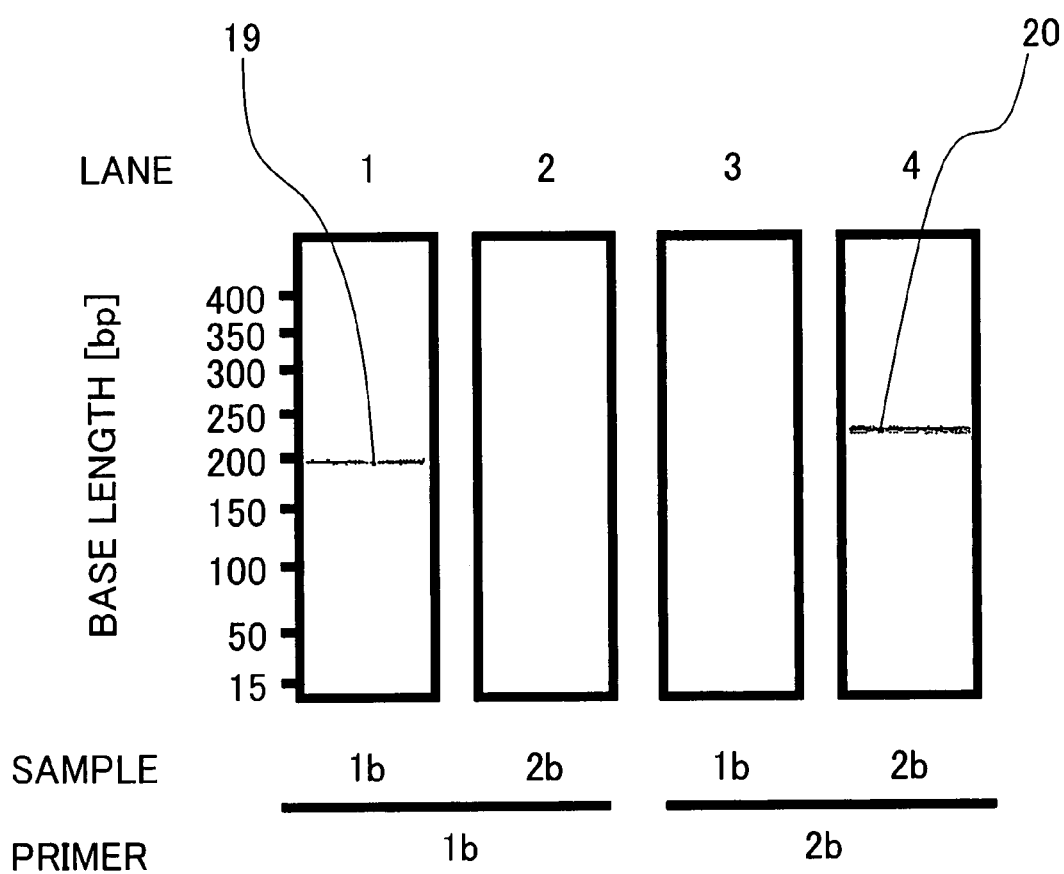
FIG. 6 shows an electropherogram obtained by genotyping of HCV subtypes 1b and 2b using oligonucleotide primers of the present invention.

FIG. 6 shows the resulting electropherogram. The oligonucleotide primers corresponding to SEQ ID NOs: 3 and 12 were so designed as to yield an amplified product having a size of amplification of 209 bp as a result of the amplification of the HCV subtype 1b RNA. The oligonucleotide primers corresponding to SEQ ID NOs: 21 and 23 were so designed as to yield an amplified product having a size of 214 bp as a result of the amplification of the HCV subtype 2b RNA.

The results of the amplification reaction with the oligonucleotide primers corresponding to SEQ ID NOs: 3 and 12 are shown in Lanes 1 and 2. The results of the amplification reaction using with oligonucleotide primers corresponding to SEQ ID NOs: 21 and 23 are shown in Lanes 3 and 4. An amplified product 19 was detected at a base length of 209 bp in Lane 1 as a result of the amplification of the HCV subtype 1b RNA as a sample. In contrast, no amplified product was detected in Lane 2 as a result of the amplification of the HCV subtype 2b as a sample. An amplified product 20 was detected at a base length of 214 bp in Lane 4 as a result of the amplification of the HCV subtype 2b RNA as a sample. In contrast, no amplified product was detected in Lane 3 as a result of the amplification of the HCV subtype 1b as a sample. These results show that the oligonucleotide primers of the present invention yield amplified products at estimated base lengths only when reacted with samples having corresponding genotypes.

The oligonucleotide primers of the present invention are usable in the detection and genotyping of hepatitis C virus and can thereby be widely used in researches on HCV, such as studies on pathoses, estimation and determination of efficacies of agents depending on the subtypes of HCV.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

SEQUENCE LISTING FREE TEXT

SEQ ID NO: 1—Description of Artificial Sequence: sense primer for the amplification of HCV subtype 1a SEQ ID NO: 2—Description of Artificial Sequence: antisense primer for the amplification of HCV subtype 1a SEQ ID NO: 3—Description of Artificial Sequence: sense primer for the amplification of HCV subtype 1b SEQ ID NO: 4—Description of Artificial Sequence: antisense primer for the amplification of HCV subtype 1b SEQ ID NO: 5—Description of Artificial Sequence: sense primer for the amplification of HCV subtype 2a SEQ ID NO: 6—Description of Artificial Sequence: antisense primer for the amplification of HCV subtype 2a SEQ ID NO: 7—Description of Artificial Sequence: sense primer for the amplification of HCV subtype 3a SEQ ID NO: 8—Description of Artificial Sequence: antisense primer for the amplification of HCV subtype 3a SEQ ID NO: 9—Description of Artificial Sequence: antisense primer for the amplification of HCV subtype 1b SEQ ID NO: 10—Description of Artificial Sequence: antisense primer for the amplification of HCV subtype 2a SEQ ID NO: 11—Description of Artificial Sequence: antisense primer with T7 promoter sequence for the amplification of HCV subtype 1a SEQ ID NO: 12—Description of Artificial Sequence: antisense primer with T7 promoter sequence for the amplification of HCV subtype 1b SEQ ID NO: 13—Description of Artificial Sequence: antisense primer with T7 promoter sequence for the amplification of HCV subtype 2a SEQ ID NO: 14—Description of Artificial Sequence: antisense primer with T7 promoter sequence for the amplification of HCV subtype 3a SEQ ID NO: 15—Description of Artificial Sequence: antisense primer with Tag sequence for the amplification of HCV subtype 1b SEQ ID NO: 16—Description of Artificial Sequence: antisense primer with Tag sequence for the amplification of HCV subtype 2a SEQ ID NO: 17—Description of Artificial Sequence: sense primer with T7 promoter sequence for the amplification of HCV subtype 1b SEQ ID NO: 18—Description of Artificial Sequence: sense primer with T7 promoter sequence for the amplification of HCV subtype 2a SEQ ID NO: 19—Description of Artificial Sequence: molecular beacon sequence with Tag sequence SEQ ID NO: 20—Description of Artificial Sequence: molecular beacon sequence with Tag sequence SEQ ID NO: 21—Description of Artificial Sequence: sense primer for the amplification of HCV subtype 2b SEQ ID NO: 22—Description of Artificial Sequence: anti-sense primer for the amplification of HCV subtype 2b SEQ ID NO: 23—Description of Artificial Sequence: anti-sense primer with T7 promoter sequence for the amplification of HCV subtype 2b SEQ ID NO: 24—Description of Artificial Sequence: HCV subtype 1a sense primer SEQ ID NO: 25—Description of Artificial Sequence: HCV subtype 1a sense primer SEQ ID NO: 26—Description of Artificial Sequence: HCV subtype 1a sense primer SEQ ID NO: 27—Description of Artificial Sequence: HCV subtype 1a sense primer SEQ ID NO: 28—Description of Artificial Sequence: HCV subtype 1a sense primer SEQ ID NO: 29—Description of Artificial Sequence: HCV subtype 1a sense primer SEQ ID NO: 30—Description of Artificial Sequence: HCV subtype 1a sense primer SEQ ID NO: 31—Description of Artificial Sequence: HCV subtype 1a sense primer SEQ ID NO: 32—Description of Artificial Sequence: HCV subtype 1a sense primer SEQ ID NO: 33—Description of Artificial Sequence: HCV subtype 1a antisense primer with T7 promoter sequence SEQ ID NO: 34—Description of Artificial Sequence: HCV subtype 1a antisense primer with T7 promoter sequence SEQ ID NO: 35—Description of Artificial Sequence: HCV subtype 1a antisense primer with T7 promoter sequence SEQ ID NO: 36—Description of Artificial Sequence: HCV subtype 1a antisense primer with T7 promoter sequence SEQ ID NO: 37—Description of Artificial Sequence: HCV subtype 1a antisense primer with T7 promoter sequence SEQ ID NO: 38—Description of Artificial Sequence: HCV subtype 1a antisense primer with T7 promoter sequence SEQ ID NO: 39—Description of Artificial Sequence: HCV subtype 1a antisense primer with T7 promoter sequence SEQ ID NO: 40—HCV subtype 1a-specific core region SEQ ID NO: 41—HCV subtype 1b-specific core region SEQ ID NO: 42—HCV subtype 2a-specific core region SEQ ID NO: 43—HCV subtype 2b-specific core region SEQ ID NO: 44—HCV subtype 3a-specific core region SEQ ID NO: 45—Description of Artificial Sequence: sequence with T7 promoter sequence

---

What is claimed is:

1. A method for detecting hepatitis C virus, comprising the steps of:
   subjecting a clinical sample to isothermal amplification with at least one pair of primers selected from the following pairs of primers (1) to (5); and
   determining a subtype of hepatitis C virus based on the resulting amplified product:
   (1) a pair of primers comprising at least eighteen consecutive bases corresponding to a 3' end region of the base sequences of SEQ ID NOs: 1 and 2, respectively;
   (2) a pair of primers comprising at least eighteen consecutive bases corresponding to a 3' end region of the base sequences of SEQ ID NOs: 3 and 4, respectively, or a pair of primers comprising at least eighteen consecutive bases corresponding to a 3' end region of the base sequences of SEQ ID NOs: 3 and 9, respectively;
   (3) a pair of primers comprising at least eighteen consecutive bases corresponding to a 3' end region of the base sequences of SEQ ID NOs: 5 and 6, respectively, having a property of being capable of genotyping hepatitis C virus subtype 2a gene, or a pair of primers comprising at least eighteen consecutive bases corresponding to a 3' end region of the base sequences of SEQ ID NOs: 5 and 10, respectively;
   (4) a pair of primers comprising at least eighteen consecutive bases corresponding to a 3' end region of the base sequences of SEQ ID NOs: 7 and 8, respectively; and
   (5) a pair of primers comprising at least eighteen consecutive bases corresponding to a 3' end region of the base sequences of SEQ ID NOs: 21 and 22, respectively.

2. The method according to claim 1, wherein at least one of the pair of primers further comprises a T7 promoter sequence.

3. The method according to claim 1, further comprising simultaneously determining two or more subtypes of hepatitis C virus with two or more pairs of primers.

* * * * *

UNITED STATES PATENT AND TRADEMARK OFFICE
CERTIFICATE OF CORRECTION

| | | |
|---|---|---|
| PATENT NO. | : 8,008,045 B2 | Page 1 of 1 |
| APPLICATION NO. | : 11/976232 | |
| DATED | : August 30, 2011 | |
| INVENTOR(S) | : Maiko Tanabe and Chihiro Uematsu | |

It is certified that error appears in the above-identified patent and that said Letters Patent is hereby corrected as shown below:

It is respectfully requested that the cover page of U.S. Patent No. 8,008,045 be corrected to contain reference to:

Foreign Application Priority Data
Japanese Application JP 2004-149448, filed on May 19, 2004, and Related U.S. Application Data
Divisional of application No. 11/132,286, filed on May 19, 2005.

It is also respectfully requested that the paragraph at column 1, lines 6-9, of U.S. Patent No. 8,008,045 be replaced by the following paragraph:

The present application is a divisional of U.S. Application No. 11/132,286, filed May 19, 2005. The present application claims priority from Japanese Application JP 2004-149448, filed May 19, 2004, the content of which is hereby incorporated by reference into this application.

Signed and Sealed this
Twenty-seventh Day of March, 2012

David J. Kappos
*Director of the United States Patent and Trademark Office*

SEQUENCE LISTING

```
<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: Inventor: Tanabe, Maiko; Uematsu, Chihiro
<220> FEATURE:
<223> OTHER INFORMATION: Description of Artificial Sequence:HCV subtype
      1a sense DNA primer

<400> SEQUENCE: 1
caccatgagc acgaatccta                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:HCV subtype
      1a anti-sense DNA primer

<400> SEQUENCE: 2
wgccttgggg ataggctg                                                      18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:HCV subtype
      1b sense DNA primer

<400> SEQUENCE: 3
caccatgagc acgaatccta                                                    20

<210> SEQ ID NO 4
<211> LENGTH: 20
```

```
<212> TYPE: DNA
<213> ORGANISM: Artificial Sequence
<220> FEATURE:
<223> OTHER INFORMATION: Description of Artificial Sequence:HCV subtype
      1b anti-sense DNA primer

<400> SEQUENCE: 4
gagccatcct gcccacccca                                                 20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:HCV subtype
      2a sense DNA primer

<400> SEQUENCE: 5
cctaaacctc aaagaaaaac ca                                              22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:HCV subtype
      2a anti-sense DNA primer

<400> SEQUENCE: 6
tggttttccc caggatttgc cagt                                            24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:HCV subtype
      3a sense DNA primer

<400> SEQUENCE: 7
yaacatgagc acacttccta                                                 20

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:HCV subtype
      3a anti-sense DNA primer

<400> SEQUENCE: 8
tycgctcyga cgcgccttgg ggata                                           25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:HCV subtype
      1b anti-sense DNA primer

<400> SEQUENCE: 9
ggataggttg tcgccatcca                                                 20

<210> SEQ ID NO 10
<211> LENGTH: 21
<212> TYPE: DNA
<213> ORGANISM: Artificial Sequence
```

```
<220> FEATURE:
<223> OTHER INFORMATION: Description of Artificial Sequence:HCV subtype
      2a anti-sense DNA primer

<400> SEQUENCE: 10
cccgtatagg ggccaggggt a                                              21

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence:HCV subtype
      1a anti-sense DNA primer with T7 promoter

<400> SEQUENCE: 11
aattctaata cgactcacta tagggagaag gwgccttggg gataggctg                49

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence:HCV subtype
      1b anti-sense DNA primer with T7 promoter

<400> SEQUENCE: 12
aattctaata cgactcacta tagggagaag ggagccatcc tgcccacccc a             51

<210> SEQ ID NO 13
<211> LENGTH: 55
<212> TYPE: DNA
<213> ORGANISM: Artificial Sequence
<220> FEATURE:
<223> OTHER INFORMATION: Description of Artificial Sequence:HCV subtype
      2a anti-sense DNA primer with T7 promoter

<400> SEQUENCE: 13
aattctaata cgactcacta tagggagaag gtggttttcc ccaggatttg ccagt         55

<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence:HCV subtype
      3a anti-sense DNA primer with T7 promoter

<400> SEQUENCE: 14
aattctaata cgactcacta tagggagaag gtycgctcyg acgcgccttg gggata        56

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence:HCV subtype
      1b anti-sense DNA primer with Tag seqence

<400> SEQUENCE: 15
ctctgttccc tcatcacttc tggataggtt gtcgccatcc a                        41

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence:HCV subtype
```

2a anti-sense DNA primer with Tag seqence

<400> SEQUENCE: 16
cactcatctc ttctccctgt tcccgtatag gggccagggg ta                    42

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence:HCV subtype
      1b sense DNA primer with T7 promoter

<400> SEQUENCE: 17
aattctaata cgactcacta tagggagaag gcaccatgag cacgaatcct a          51

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence:HCV subtype
      2a sense DNA primer with T7 promoter

<400> SEQUENCE: 18
aattctaata cgactcacta tagggagaag gcctaaacct caaagaaaaa cca        53

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:Molecular
      beacon probe for detection of Tag seqence

<400> SEQUENCE: 19
cgacgtctct gttccctcat cacttctacg tcg                              33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:Molecular
      beacon probe for detection of Tag seqence

<400> SEQUENCE: 20
cgacgtcact catctcttct ccctgttacg tcg                              33

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:HCV subtype
      2b sense DNA primer

<400> SEQUENCE: 21
aagttcccgg gyggcggyca gat                                         23

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:HCV subtype
      2b anti-sense DNA primer

```
<400> SEQUENCE: 22
arccctcgtt tccgtacagr ggccaa                                    26

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence:HCV subtype
      2b anti-sense DNA primer with T7 promoter

<400> SEQUENCE: 23
aattctaata cgactcacta tagggagaag garccctcgt ttccgtacag rggccaa   57

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 24
gaggtctcgt agaccgtgca cca                                       23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 25
tcagatcgtt ggtggagttt a                                         21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 26
tcgttggtgg agtttacttg tt                                        22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 27
aggaagactt ccgagcggtc                                           20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 28
```

```
ggaagacttc cgagcggtcg ca                                              22
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 29

```
cctaaacctc aaagaaaaac ca                                              22
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 30

```
ccaaacgtaa caccaaccgt                                                 20
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 31

```
agttcccggg tggcggtcag                                                 20
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:HCV subtype
      1a sense DNA primer

<400> SEQUENCE: 32

```
agacttccga gcggtcgcaa c                                               21
```

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence:HCV subtype
      1a anti-sense DNA primer with T7 promoter

<400> SEQUENCE: 33

```
aattctaata cgactcacta tagggagaag gaacttgacg tcctgtgggc ga             52
```

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence:HCV subtype
      1a anti-sense DNA primer with T7 promoter

<400> SEQUENCE: 34

```
aattctaata cgactcacta tagggagaag gaaactccac caacgatctg a              51
```

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence:HCV subtype
    1a anti-sense DNA primer with T7 promoter

<400> SEQUENCE: 35
aattctaata cgactcacta tagggagaag gtgccttggg gataggctgg cgtcta           56

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence:HCV subtype
    1a anti-sense DNA primer with T7 promoter

<400> SEQUENCE: 36
aattctaata cgactcacta tagggagaag gacggttggt gttacgtttg g                51

<210> SEQ ID NO 37
<211> LENGTH: 52
<212> TYPE: DNA
<213> ORGANISM: Artificial Sequence
<220> FEATURE:
<223> OTHER INFORMATION: Description of Artificial Sequence:HCV subtype
    1a anti-sense DNA primer with T7 promoter

<400> SEQUENCE: 37
aattctaata cgactcacta tagggagaag gggcgtctac ctcgaggttg cg               52

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence:HCV subtype
    1a anti-sense DNA primer with T7 promoter

<400> SEQUENCE: 38
aattctaata cgactcacta tagggagaag gtacctcgag gttgcgaccg ctcgga           56

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence:HCV subtype
    1a anti-sense DNA primer with T7 promoter

<400> SEQUENCE: 39
aattctaata cgactcacta tagggagaag ggccgacgtg ccttgggga                   49

<210> SEQ ID NO 40
<211> LENGTH: 238
<212> TYPE: DNA
<213> ORGANISM: Artificial Sequence
<220> FEATURE:
<223> OTHER INFORMATION: Description of Artificial Sequence:HCV subtype
    1a sequence for designing primer pairs

<400> SEQUENCE: 40
gggaggtctc gtagaccgtg caccatgagc acgaatccta aacctcaaag aaaaaccaaa       60
cgtaacacca accgtcgccc acaggacgtc aagttcccgg gtggcggtca gatcgttggt      120

-continued

```
ggagtttact tgttgccgcg caggggccct agattaggtg tgcgcgcgac gaggaagact    180
tccgagcggt cgcaacctcg aggtagacgc cagcctatcc ccaaggcacg tcggcccg     238

<210> SEQ ID NO 41
<211> LENGTH: 325
<212> TYPE: DNA
<213> ORGANISM: Artificial Sequence
<220> FEATURE:
<223> OTHER INFORMATION: Description of Artificial Sequence:HCV subtype
      1b sequence for designing primer pairs

<400> SEQUENCE: 41
gggaggtctc gtagaccgtg caccatgagc acgaatccta aacctcaaag aaaaaccaaa    60
cgtaacacca accgccgccc acaggacgtc aagttcccgg gcggtggtca gatcgttggt   120
ggagtttacc tgttgccgcg caggggcccc aggttgggtg tgcgcgcgac taggaagact   180
tccgagcggt cgcaacctcg tggatggcga caacctatcc ccaaggctcg ccgacccgag   240
ggcagggcct gggctcagcc cgggtaccct tggcccctct atggcaatga gggcttgggg   300
tgggcaggat ggctcctgtc acccc                                         325

<210> SEQ ID NO 42
<211> LENGTH: 275
<212> TYPE: DNA
<213> ORGANISM: Artificial Sequence
<220> FEATURE:
<223> OTHER INFORMATION: Description of Artificial Sequence:HCV subtype
      2a sequence for designing primer pairs

<400> SEQUENCE: 42
caccatgagc acaaatccta aacctcaaag aaaaaccaaa agaaacacca accgtcgccc    60
acaagacgtt aagtttccgg gcggcggcca gatcgttggc ggagtatact tgttgccgcg   120
caggggcccc aggttgggtg tgcgcgcgac aaggaagact tcggagcggt cccagccacg   180
tggaaggcgc cagcccatcc ctaaggatcg gcgctccact ggcaaatcct ggggaaaacc   240 aggataccccc tggccccctat acgggaatga gggac                            275

<210> SEQ ID NO 43
<211> LENGTH: 305
<212> TYPE: DNA
<213> ORGANISM: Artificial Sequence
<220> FEATURE:
<223> OTHER INFORMATION: Description of Artificial Sequence:HCV subtype
      2b sequence for designing primer pairs

<400> SEQUENCE: 43
gggaggtctc gtagaccgtg catcatgagc acaaatccta aacctcaaag aaaaaccaaa    60
agaaacacaa accgccgccc acaggacgtc aagttcccgg gcggcggcca gatcgttggc   120
ggagtttact tgctgccgcg caggggcccc aggttgggtg tgcgcgcgac gaggaagact   180
tccgagcgat cccagccgcg tgggaggcgc cagcccatcc cgaaagatcg gcgctccacc   240
ggcaagtcct ggggaaagcc aggatatcct tggcctctgt acggaaacga gggctgcggc   300
tggca                                                               305

<210> SEQ ID NO 44
<211> LENGTH: 366
<212> TYPE: DNA
<213> ORGANISM: Artificial Sequence
<220> FEATURE:
<223> OTHER INFORMATION: Description of Artificial Sequence:HCV subtype
      3a sequence for designing primer pairs
```

-continued

```
<400> SEQUENCE: 44
gggaggtctc gtagaccgtg caacatgagc acacttccta aacctcaaag aaaaaccaaa        60
agaaacaccg tccgtcgccc acaggacgtc aagttcccgg gtggcggaca gatcgttggt       120
ggagtatacg tgctgccgcg caggggccca cgcttgggtg tgcgcgcgac gcgtaaaact       180
tctgaacggt cacagcctcg cggacgacga cagcctatcc ccaaggcgcg tcggagcgaa       240
ggccggtcct gggctcagcc tgggtaccct tggcccctct atggtaacga gggctgcggg       300
tgggcaggat ggctcctgtc cccacgcggc tcccgtccat cttggggccc aaacgacccc       360
cggcgg                                                                  366

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: The
      sequence including T7 promoter sequence

<400> SEQUENCE: 45
aattctaata cgactcacta tagggagaag g                                       31
```